United States Patent [19]

Knowles et al.

[11] Patent Number: 4,658,022

[45] Date of Patent: Apr. 14, 1987

[54] BINDING OF ANTIBODY REAGENTS TO DENATURED PROTEIN ANALYTES

[75] Inventors: William J. Knowles, Hamden; Vincent T. Marchesi, Gulford, both of Conn.

[73] Assignee: Molecular Diagnostics, Inc., West Haven, Conn.

[21] Appl. No.: 779,730

[22] Filed: Sep. 27, 1985

Related U.S. Application Data

[63] Continuation-in-part of Ser. No. 763,193, Aug. 8, 1985, which is a continuation-in-part of Ser. No. 665,811, Oct. 29, 1984, abandoned.

[51] Int. Cl.⁴ ..................... A61K 39/00; G01N 33/56
[52] U.S. Cl. ................................. 530/402; 530/362; 530/363; 530/380; 530/395; 530/808; 424/88; 424/89; 435/7; 436/514; 436/548; 436/86; 436/87; 436/819
[58] Field of Search ...................... 260/112 R, 112 B; 424/85, 86, 87, 88, 89, 402; 530/350, 362, 363, 395, 380, 808; 435/7; 436/514, 548, 86, 87, 819

[56] References Cited

U.S. PATENT DOCUMENTS

4,247,533  1/1981  Cerami et al. ................ 260/112.5 R
4,423,034  12/1983  Nakagawa et al. .......... 260/112.5 R
4,478,744  10/1984  Mezei et al. ............................. 424/1

FOREIGN PATENT DOCUMENTS

0111211  6/1984  European Pat. Off.
1580318  12/1980  United Kingdom.

OTHER PUBLICATIONS

Clinical Chemistry, vol. 30, No. 11, Nov. 1984, pp. 1746-1752.

Primary Examiner—Morton Foelak
Assistant Examiner—Nathan M. Nutter
Attorney, Agent, or Firm—Sprung Horn Kramer & Woods

[57] ABSTRACT

Binding of a particular protein by an antibody reagent involving denaturation of the protein and use of an antibody reagent specific for binding a linear peptide epitope therein. Denaturation by chemical or physical means effectively exposes or enhances the exposure of the linear peptide epitope for binding by the antibody reagent which is preferably raised against a synthetic peptide immunogen. The technique is particularly useful in performing immunoassays for protein analytes, such as a glycosylated protein, in aqueous test samples.

69 Claims, 9 Drawing Figures

BINDING OF ANTIBODY REAGENTS TO DENATURED PROTEIN ANALYTES

CROSS-REFERENCE TO RELATED APPLICATIONS

This application is a continuation-in-part application of application Ser. No. 763,193, filed Aug. 8, 1985, now pending, which is a continuation-in-part application of application Ser. No. 665,811, filed Oct. 29, 1984, now abandoned.

BACKGROUND OF THE INVENTION

This invention relates to methods for binding a protein with an antibody reagent such as is accomplished in the performance of immunoassays. In particular, the invention concerns the binding of antibodies, fragments thereof and the like, to specific linear peptide epitopes in proteins and polypeptides.

There is a continuing need to improve the specificity of antibody binding to proteins, particularly proteins of analytical significance. The specific detection of particular proteins in biological samples such as blood is limited by the ability to obtain antibody reagents directed to unique binding sites or epitopes on the accessible portions of the proteins. There are situations where the most desirable epitope for specific detection of a particular protein is inaccessible or has only limited accessibility for binding to an antibody reagent.

An example is the determination of the glucosylated form of hemoglobin known as Hb Alc in blood samples of diabetic patients. Hemoglobin is a protein tetramer made up of four chains (subunits) of amino acids, each of about 143 units and having a total molecular weight of about 64,000. At one end of the molecule (the $NH_2$-terminus of the beta-subunit) there is a valine unit which can react with glucose. The glucosylation of hemoglobin occurs by a non-enzymatic reaction involving glucose and the alpha-amino group of valine. Following a Schiff base formation between the reactants, the glucose undergoes an Amadori rearrangement forming 1-deoxyfructo-valine. This complex is covalent and essentially irreversible. The glucosylation reaction is governed by the concentration of the reactants, e.g., hemoglobin and glucose. In a normal (non-diabetic) individual approximately 3% of the total hemoglobin is glucosylated. Hemoglobin tetramers with a 1-deoxyfructo-valine on the N-terminus of a beta-chain are identified as being glucosylated or $A_{1c}$ hemoglobin.

Glucose levels in diabetics are sufficiently high to increase the rate of glucosylation in direct dependence upon the glucose level in the blood, which reflects the severity of the diabetic condition. With hemoglobin, the $A_{1c}$ level is raised to about 5 to 12%. Since the circulating life span of hemoglobin is about 120 days, a glucosylated hemoglobin measurement will give a value which reflects an average glucose level for that period. Notably a meal high in glucose will not be reflected in a high glucosylated hemoglobin or serum albumin level. Thus, measurement of the glucosylated hemoglobin content gives a truer picture of the average circulating glucose levels and thus a truer picture of the long term condition of the patient.

U.S. Pat. No. 4,247,533 discloses an analytical technique wherein antibodies to Hb $A_{1c}$ were reportedly raised in a special sheep by injection of Hb $A_{1c}$ and absorbed with nonglucosylated hemoglobin to provide polyclonal antibodies which distinguished between Hb $A_{1c}$ and nonglucosylated Hb. Such antibodies then form the basis for a test to determine the proportion of glucosylated hemoglobin in a sample. The test, however, requires an appropriately immunized sheep and antibody absorptions to attain the proper specificity. It is, therefore, costly and difficult to produce specific polyclonal antibodies. The antibody preparations produced by this absorption approach are reported to be of low titer and affinity. The reproducibility of this approach is also open to question since there are no recent reports describing its use for the analysis of clinical samples of human hemoglobin.

Another attempt to obtain antibodies specific for Hb $A_{1c}$ id found in U.S. Pat. No. 4,478,744. These workers substituted a synthetic peptide immunogen for the normal hemoglobin molecule as the immunizing agent. This material was injected into an animal which normally does not have Hb $A_{1c}$ in its bloodstream, e.g., sheep. The synthetic peptide immunogen comprised a glucosylated peptide residue having an amino acid sequence corresponding to between the first 4 to 10 amino acids in the N-terminal hemoglobin sequence. Subsequent investigations, reported hereinbelow, have found that the sheep polyclonal antiserum raised against the synthetic peptide immunogen has no detectable specificity for the glucosylated form, Hb $A_{1c}$.

Therefore, there is an unsatisfied need to develop an approach to designing antibody reagents and binding conditions that permit the specific binding of antibody reagents to proteins of interest. This is particularly apparent from the inability of prior workers to devise immunoassays for the determination of particular proteins such as glycosylated proteins, e.g., Hb $A_{1c}$.

| Definitions | |
|---|---|
| Amino Acid | Abbreviation |
| Arginine | Arg |
| Asparatic Acid | Asp |
| Glutamic Acid | Glu |
| Lysine | Lys |
| Serine | Ser |
| Asparagine | Asn |
| Glutamine | Gln |
| Glycine | Gly |
| Proline | Pro |
| Threonine | Thr |
| Alanine | Ala |
| Histidine | His |
| Cysteine | Cys |
| Methionine | Met |
| Valine | Val |
| Isoleucine | Ile |
| Leucine | Leu |
| Tyrosine | Tyr |
| Phenylalanine | Phe |
| Tryptophan | Trp |

SUMMARY OF THE INVENTION

It has now been found that highly specific immunobinding to a particular protein can be achieved by forming an antibody reagent against a linear peptide epitope in the protein and contacting such antibody reagent with the protein after denaturing the protein sufficiently to expose or increase the exposure of the linear peptide epitope therein. The targeted linear peptide epitope will in principle comprise at least two, and usually less than 15, amino acid units. The epitope can appear at an N- or C-terminus of a peptide chain or can appear along the peptide chain in the protein, and can be modified with non-peptide groups and side-chains such as carbohydrates, including mono-, oligo-, and polysaccharide groups, phosphates, lipids, sulfates, carbamyl, sulfoxide, and the like, including other chemical groups that may be found covalently attached to the protein backbone. Such groups include those added by post-translational modifications which can be enzyme mediated or the result of non-enzymatic chemical reaction, therefore including modifications which occur naturally in the protein or which are caused by environmental exposure. The antibody reagent will normally be raised against a synthetic peptide comprising the linear peptide epitope linked to an immunogenic carrier material, usually different from the protein of interest. It will be particularly preferred to employ somatic cell hybridization techniques to obtain antibodies which are monoclonal and selected for high specificity for the linear peptide epitope.

The denaturation of the protein can be accomplished in essentially any manner so as to expose or increase the exposure of the selected peptide epitope for antibody binding while maintaining a significant amount of the protein in solution. Physical or chemical treatments, the latter including protein digestion, are available for selection of the optimal denaturation conditions. The degree or extent of denaturation necessary will be determined essentially empirically for each protein and for each intended applicatiion of the resulting immunobinding, e.g., the conditions of a desired immunoassay. The effect of denaturation is to substantially linearize at least the region of the protein in which the selected peptide epitope occurs and to expose it to the surrounding aqueous medium sufficient for binding to the antibody reagent.

The present invention enables the performance of immunoassays and the preparation of reagent systems for determining proteins by binding of the antibody reagent to linear peptide epitopes that are substantially inaccessible to or have limited accessibility for immunobinding when the protein is in its native state. In particular, means are provided for the highly specific determination of glucosylated proteins such as glucosylated hemoglobin and albumin, and particularly Hb $A_{1c}$ in biological fluids such as blood. Monoclonal antibodies raised against the synthetic glucosylated N-terminal peptide residues appearing in Hb $A_{1c}$ have been found to bind specifically to such residues in the glucosylated beta-subunit of hemoglobin. The antibodies can be prepared in a variety of manners following conventional monoclonal techniques. Principally, the antibodies are prepared against a synthetically derived immunogen comprising the desired glucosylated N-terminal peptide residue chemically linked to an immunogenic carrier, the glucosylated peptide having at least 2, and preferably from about 5 to 15, amino acid units corresponding to Hb $A_{1c}$. The resultant antibodies are specific for the glucosylated synthetic peptide and the corresponding exposed epitope in the hemoglobin $A_{1c}$ molecule.

BRIEF DESCRIPTION OF THE DRAWINGS

The drawings are graphs presenting data from experiments described in the Examples below relating to the immunodetection of Hb $A_{1c}$.

DESCRIPTION OF THE PREFERRED EMBODIMENTS

Figure 1:
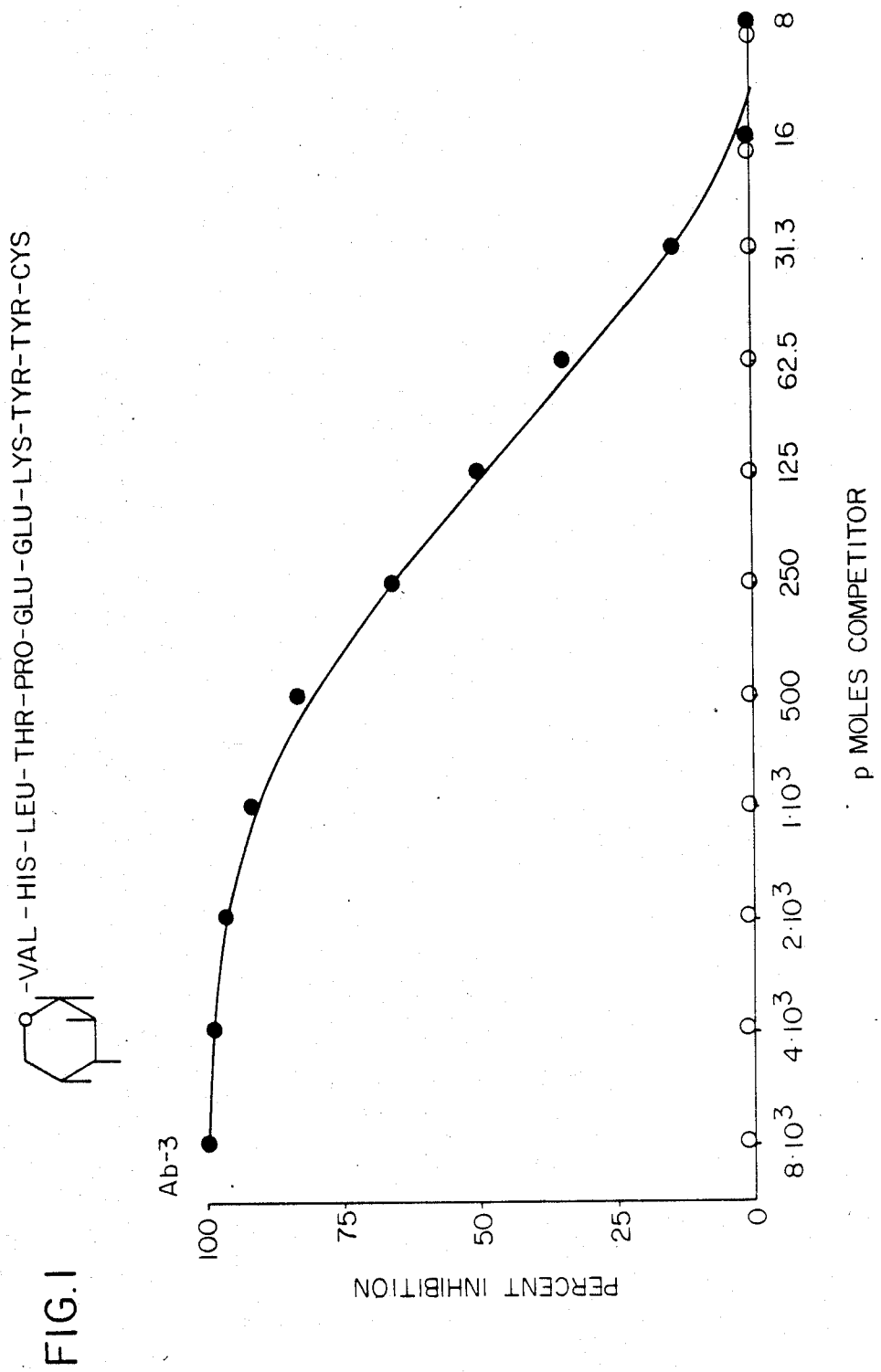
FIG. 1 is a plot depicting the inhibition of Ab-3 binding to $A_{1c}$ by glycopeptide 1 (PEPTIDE 1). Antibody was preincubated with glycopeptide before transfer into an $A_{1c}$ coated microtiter plate. The monoclonal antibody that binds to $A_{1c}$ was detected using a secondary antibody-enzyme. The results are plotted in FIG. 1 as a present inhibition where 0% inhibition is the value obtained with no competitor. The 0—0 line is from an identical peptide that lacks the carbohydrate, indicating the carbohydrate is essential for antibody binding. All points are the mean of triplicate measurements.

A polypeptide or protein exists as a linear sequence of amino acids which in solution forms a three dimensional structure. The factors which control the spontaneous acquisition of this 3-dimensional structure of a protein include the following:

1. The planar structure of the peptide bond having limited rotation around the $C^\alpha$ and $C'$ carbon atoms ($\Psi$ bond rotation) and around the $N-C^\alpha$ nitrogen-carbon bond ($\phi$ bond rotation). This limited rotation restricts movement around the peptide bond and reduces the total number of possible conformations.
2. The amino acid side chains (R-groups) have a trans orientation since in all cis-polypeptide would have a severe restriction of the available conformation space for the side chain atoms.
3. Interactions between different functional groups of the peptide backbone and side chain are responsible for the 3-dimensional folding of a polypeptide and the sum of these interactions provide the energy by which the protein retains this conformation.

These interactions include:
(a) dispersion forces—where oscillating dipoles couple between adjacent atoms producing an attractive force between the two atoms. These forces are counterbalanced by the repulsion of the electronic shells (i.e., no two atoms can occupy the same space).

(b) hydrogen bonding—where the entire electron shell of a hydrogen atom shifts onto the atom to which the hydrogen is bound (hydrogen acceptor).

(c) electrostatic forces—where different types of atoms have an asymmetrical electron distribution and thereby carry a partial charge which can interact with atoms carrying an opposite charge. This interaction can be a simple dipole interaction or can exist as a salt bridge.

(d) disulfide bonds—between SH groups of cysteine amino acids stabilize protein conformation. The formation of disulfide bond is secondary to the 3-dimensional folding of the protein initiated by the dispersion forces, hydrogen bonding and electrostatic forces described above.

4. Interaction of the protein with the aqueous environment has a powerful effect in organizing the self-assembly of water-soluble proteins. The polar water molecules solvate hydrophobic groups on the surface of the protein and thermodynamically favor the sequestration of hydrophobic amino acid side chains into the interior of the molecule (so that they are in a similar hydrophobic environment). In a recent survey of known proteins the hydrophobic amino acids Phe, Leu, Ile, Val, Trp, and Tyr have more of their surface area buried than do neutral or polar amino acids (Science 229:834–838, 1985).

It should also be noted that many of the residues on the protein surface are hydrophobic and that buried residues can be polar or even charged. The buried polar groups usually satisfy hydrogen binding requirements in the protein interior and as many as 90% of all internal polar groups are involved in hydrogen bonds. Likewise charged amino acids in the protein interior are most likely involved in salt bridges.

The conformation of a protein can be divided into a hierarchy of structure as follows:

1. Primary structure is the linear amino acid sequence of the polypeptide.
2. Secondary structure refers to the manner in which the polypeptide chain is stabilized by hydrogen bonding.
3. Tertiary structure is the folding of the polypeptide chain into its three dimensional structure. This structure is stabilized by hydrogen bonds, electrostatic interactions, hydrophobic interactions and by disulfide bonds.
4. Quaternary structure refers to the structure formed when two polypeptide chains interact. The types of interactions are the same as for tertiary structure.

The described interactions of the polypeptide with polypeptide and with the aqueous environment are responsible for the complex folding and the resulting three-dimensional structure of nature protein molecules. The information for this folding is encoded in the amino acid sequence of the polypeptide (the primary structure). In many instances native proteins can be totally denatured (evidenced by a lack of secondary, tertiary and quaternary structure) by treatment with physical or chemical denaturants and upon removal of the denaturant, will refold into a molecule that is indistinguishable in structure and function from the native protein (Adv. Prot. Chem. 29:205–299, 1975; Journal of Biol. Chem. 251:3154–3157, 1976).

The folding process is energetically favored and the resulting native three-dimensional conformation is at (or at least close to) its minimal free energy state. As a consequence of the folding of the polypeptide into a three-dimensional conformation, some amino acids are on the surface of the molecule freely accessible to the suspending solvent whereas other amino acids are buried and are inaccessible to solvent. This concept is supported by a large amount of biophysical data and also by the differences in chemical reactivities of amino acids on the protein surface versus those in the protein interior.

The three-dimensional conformation is by no means a rigid structure. Most of the previously described interactions are relatively weak and are constantly breaking and reforming (however at any one time only a small percentage of the total bonds are broken). One might except that peptide segments with the fewest interactions would have greater mobility than peptide segments with a greater number of interactions. The segments with greater mobility could assume a greater number of conformations, one of which may be capable of interaction with an antibody. It has been suggested that these mobile portions of native proteins are those that are most antigenic (Nature 312:127–134, 1984).

The interactions between an antigen and antibody are the same as those that stabilize protein structure (i.e., hydrogen, electrostatic, hydrophobic bonds). For the interaction to be specific and of sufficient affinity, it is necessary to maintain complementarity of the two interacting surfaces and a suitable juxtaposition of oppositely charged groups forming salt bridges, hydrogen bond donors and acceptors and hydrophobic pockets (Ann. Rev. Immunol 1:87–117, 1983). If the complementarity is changed (e.g., amino acid substitution), the affinity of the antibody for the antigen can be dramatically altered.

The contact sites on the antigen can be divided into two groups (1) linear or sequential and (2) conformational (Ann Rev. Immunol. 2:67–101, 1984).

Linear or sequential determinants are those in which the entire antigenic determinant is found on a single linear segment of the protein sequence that ranges from approximately two to 15 amino acids, and commonly having less than 10 amino acids.

Conformational determinants are those in which portions of the peptide, distant in sequence, are brought into close contact by the three-dimensional folding of the protein antigen. Therefore, the antigen determinant or epitope is formed from more than one portion of the protein antigen. For example X-ray diffraction studies with lysozyme and a monoclonal antibody against lysozyme have shown that the antibody contacts lysozyme at positions 29–37 and 116–129. Although these amino acids are separate in sequence, they form a continguous patch approximately 20×25A on the surface of the lysozyme molecule, and interact with multiple atoms of the antibody combining site (Nature 313:156–158, 1985). It also follows that antibodies that recognize conformational determinants will not recognize the denatured form of the protein.

In the conventional procedure of immunization for generating an anti-protein antibody, a native or seminative protein is injected into an animal, which in time produces immunoglobulins against the immunogen. A polyclonal antiserum most likely contains antibodies that recognize both sequential and conformational antigenic determinants. These determinants are most likely located on the surface of the native protein. For example, the haemagglutin membrane glycoprotein of influenza virus has four major antigenic determinants three of which have been localized to the surface of the glycoprotein (Nature 289:366-373 and 373-378, 1981).

If a synthetic peptide or a small peptide from the native molecule is used as the immunogen, the resulting response can only be against the sequential determinants (and the limited number of conformations that the peptide can attain). In attempts to use synthetic peptides as immumogens to produce an antibody response which will bind to the native protein (having the same sequence as the synthetic peptide) investigators initially designed immunogens by searching through the sequence of the native protein for regions that had several polar amino acids (Rev-Science 229: 932-940, 1985). These sequences should statistically have a greater probability of being on the surface of the native protein and might be free to react with the antibody molecules. However, it was also thought that these hydrophilic residues would be less immunogenic than a hydrophobic peptide so others synthesized immunogens based on the hydrophobicity hoping that these hydrophobic sequences would be exposed on the surface antigens. In both cases a high proportion of the antibodies produced by these strategies react with the apparently native antigen suggesting that as long as the synthetic peptide corresponded to a sequence that could be found on the surface of a native protein, then the antibody raised against the synthetic peptide would be reactive with the native antigen (Nature 299: 592-596, 1982). There have been some reports of antibodies produced against certain synthetic peptides corresponding to peptides understood to be buried within the protein that will react with the apparently native protein (PNAS 80: 4949-4953, 1983). It is unclear what mechanism might be responsibe for this observation.

In accordance with the present invention, a native protein is purposefully denatured to optimally expose sequential or linear antigenic determinants so as to interact with antibodies that were produced against such determinants. In particular, in an assay that requires a fresh sample containing the truly native antigen, then denaturation of the antigen would be an absolute requirement. If the epitope of the native protein is at or near the surface and is therefore partially exposed to antibody interaction, denaturing can increase its mobility and result in an increase in the number of possible conformations it may attain and thereby accelerating the antibody-antigen interaction.

Many existing immunoassay formats include the use of low concentrations of detergents, e.g., Triton and Tween-20, to prevent non-specific adsorption of the reactants in the classical antibody antigen reaction, to dissociate proteins from biological membranes, or to dissociate lipids from lipoproteins providing a homogeneous sample of delipidized protein (Biochem. Biophys. Acta 620: 447-453, 1980; Clin. Chem. 28: 199-204, 1981). It is the expressed purpose of the present invention to expose the protein or glycoprotein determinant of a protein antigen by denaturing the secondary, tertiary and quaternary structure of the native protein using physical and/or chemical denaturants. The exposed peptide epitope is then unrestrained and can assume the conformations of the synthetic peptide to which the antibodies were produced.

Steric access of the antibody reagent to the epitope can be obtained in any effective manner. Exposure of the epitope in the intact protein is understood to be accomplished by a physical or chemical denaturation or digestion at least in the region of the epitope. Such denaturation or digestion can be localized to the region of the epitope or can involve a more general, or even substantially complete denaturation of the tertiary, and additionally the secondary, structure of the protein, or partial or complete digestion of the protein.

Denaturation can be accomplished in a variety of ways including conventional treatment of the protein by physical means such as heat, sonication, high or low pH and, as is preferable, chemical denaturation by digestion or interaction with a chaotropic agent or chaotrope in solution. Useful chaotropic agents include, without limitation, guanidine, urea, and various detergents such as sodium dodecylsulfate (SDS) and others, without limitation, including deoxycholate and certain bile salts, 3-(3-cholamidopropyl)-dimethyl-ammonio-1-propanesulfonate, organic solvents such as methanol, propanol, acetonitrile and certain salts such as potassium thiocyanate. Non-ionic detergents such as Triton X, Tween, nonidet NP-40 and octyl-glucosides can also function as protein denaturants. Inclusion of reagents (e.g., mercaptoethanol or dithiothrietol) that reduce disulfide bonds can be effective promoters of the denaturation process. Protein denaturation can be most effectively accomplished if combinations of chemical and/or chemical and physical means are used (e.g., guanidine and heat, guanidine and SDS, or guanidine and dithiothreitol). Particularly strong chaotropes such as guanidine are most preferred. Of course, denaturing conditions which result in substantial aggregation, insolubilization, or precipitation of the protein such that an insignificant amount of the exposed epitope is accessible to the solution for antibody binding will be avoided. A sufficient amount of the denatured protein must remain in solution or suspension in order to obtain useful immunobinding. The extent of solubilization necessary will depend upon the properties of the protein analyte and circumstances of the intended or desired binding.

A significant amount of a desired protein in a particular test sample can be denatured to expose the peptide epitope for antibody binding by combining the sample with an aqueous solution of the chaotrope present at sufficient concentration to denature a significant amount of the protein in the resulting aqueous mixture. Where whole blood is the sample as in the determination of Hb $A_{1c}$, the chaotrope also serves to lyse red blood cells, to release Hb and to inactivate proteases. In the case of guanidine, the concentration in the mixture will preferably be greater than about one molar, with about 3 molar concentration being particularly useful. The denaturation process is significantly accelerated by heating the mixture for a short period of time. It has been found that at temperatures below 37° C., denaturation by the chaotrope can take from one to several hours, whereas at temperatures above 50° C. sufficient denaturation can be attained in a minute or less. In order to prevent significant denaturation of the antibody and other proteinaceous reagents to be subsequently added to the mixture, the sample-chaotrope mixture will normally be diluted as a separate step or by addition of reagent solutions to a level that the chaotrope is substantially ineffective to denature such reagents, yet will preserve the exposure of the epitope by preventing significant renaturation of the protein of interest. For guanidine, this preferably requires dilution to a concentration less than about 1.0 molar, with about 0.3 molar being particularly preferred.

Non-limiting examples of proteolytic enzymes for use in the present invention for digestion including trypsin, chymotrypsin, proline-specific endoprotease, pepsin and papain. In performing an immunoassay, inhibitors for the proteolytic enzymes, as are known, are added to the assay mixture sufficient to prevent digestion of proteinaceous assay agents.

The present invention can be applied to essentially any desired protein, including those having lower molecular weights, e.g., 5000 daltons or less (as used herein, the term protein shall include those compounds which might be referred to as polypeptides because of their molecular weight), as well as those having molecular weights of several hundred thousand or more. Representative classes of proteins include protamines, mucoproteins, glycoproteins, globulins, albumins, phosphoproteins, histones, lipoproteins, chromoproteins, and nucleoproteins. A particularly advantageous feature of the present invention is that it provides a general approach to improving the specificity of binding and detection of proteins of analytical interest such as in the fields of medical and veterinary diagnostics. The present invention provides an opportunity to screen the otherwise inaccessible or cryptic linear peptide fragments or regions in a protein for epitopes that can afford high degrees of immunogenicity as well as specificity and advidity of antibody binding. Applications of the present invention therefore include any situation in which it is desired to bind a particular protein with an antibody reagent and which lends itself to denaturing conditions for the protein.

The present invention is particularly applicable to immunoassays and reagent systems for the specific determination of particular protein analytes. The present invention will afford the opportunity to find new and useful linear peptide epitopes and to increase the accessibility of such epitopes in proteins of interest. It will find particular application in the detection of proteins characterized by non-peptide modifications of biological or analytical significance. The present method provides an approach for designing an antibody reagent and establishing binding conditions to enable successful or improved specific detection of the protein in cases where the characterizing epitope is inaccessible or only limitedly accessible to antibody binding in the native protein. Examples of such proteins, particularly in the medical and diagnostic fields, will suggest themselves and include glycosylated proteins such as glucosylated hemoglobin (e.g., Hb Alc) and glucosylated albumin. Another application of this invention will be in finding epitopes in proteins which are more specific and/or having higher binding affinities than those available for antibody formation and binding on the normally exposed portions of the protein. By immunizing a desired host animal with a suitably denatured form of a protein or a fragment thereof, one can then examine the resulting immune response for antibodies exhibiting the desired increased specificity and/or avidity. An extension of this application is in the specific detection of cellular analytes such as blood cells, microorganisms including bacteria and viruses, and the like. In cases where it is desirable to improve the specificity of detection over that afforded by antibody binding to surface protein antigens, one can examine the internal epitopes by denaturing the surface proteins and/or proteins within the cell to look for improved antibody response.

The immunoassay determination of a protein analyte using the present antibody reagent specific for a linear peptide epitope with denaturation of the protein analyte in the test sample or assay medium can follow essentially any conventional technique. Such include the more classical techniques such as immunodiffusion, immunoelectrophoresis, agglutination techniques, and complement fixation, as well as more current techniques involving the use of specifically detectable labels such as radioimmunoassay and nonradioisotopic methods. The performance of an immunoassay for a protein analyte employing the present invention involves the essential steps of treating the aqueous test sample involved to effectively denature a significant amount of any such protein therein to expose the desired linear peptide epitope, contacting the denatured sample with the antibody reagent, and determining binding of the antibody reagent to such protein. The determination step will of course vary according to the basic immunoassay technique involved. A common technique for making this determination involves the use of a labeled reagent which interacts with either the analyte or antibody reagent and is employed in a manner to indicate the formation of immune complex between analyte and the antibody reagent or to compete with such formation.

The latter techniques can be practiced in a wide variety of formats such as the competitive binding format in which a labeled reagent is made to compete with the protein analyte for binding to the antibody reagent. The amount of labeled reagent bound to the antibody reagent, or the free-species, consisting of the labeled reagent which is not so bound, is measured appropriately and can be functionally related to the amount of protein analyte in the sample. Since the antibody reagent of the present invention is directed to a linear epitope in the protein analyte, the labeled reagent can be a labeled form of the denatured protein or a denatured fragment thereof, or, as would be preferred, a labeled form of a peptide residue comprising the linear epitope sequence of amino acids. The latter, preferred reagent can be prepared by available synthetic peptide methods and apparatus and does not require isolation, purification, and denaturation of the protein molecule itself.

Another useful immunoassay technique for the detection of protein analytes is that known as the sandwich technique. In this method, one would employ two sets of antibody reagents, one of which would be labeled and the other would be adapted to effect separation of ultimately labeled first antibody reagent bound to the protein analyte from that which is unbound. The unlabeled second antibody reagent typically is in an immobilized or immobilizable form as is known in the art.

In radioimmunoassays, the free-species and bound-species must be physically distinguished or separated in order to measure the label since the signal generated by the label is qualitatively the same in both species. Such a technique is known in the art as heterogeneous because of the phase separation requirement. Other heterogeneous immunoassay techniques are known including enzyme-labeled immunoassays, sometimes referred to as ELISA techniques (see U.S. Pat. No. 3,654,090), and fluorescent immunoassays (see U.S. Pat. Nos. 4,201,763; 4,133,639 and 3,992,631).

Fairly recently, numerous immunoassay techniques have been developed which obviate the separation step through the use of a label whose detectable signal is modulated upon binding of the labeled reagent by a binding partner, e.g., antibody. Such techniques have become known as homogeneous and when available are preferred for use in the present invention because separations are not required and radioisotopes are not involved. Some such techiques are fluorescence quenching and enhancement (see U.S. Pat. No. 4,160,016), energy transfer immunoassay (see U.S. Pat. No. 3,996,345), and double antibody steric hindrance immunoassay (see U.S. Pat. Nos. 3,935,074 and 3,998,943). Particularly preferred homogeneous immunoassay techniques are those employing a label which is a participant in an enzyme-catalyzed reaction. Examples are the substrate-labeled immunoassay (see U.S. Pat. No. 4,279,992 and U.K. Patent Spec. No. 1,552,607), the prosthetic group (FAD)-labeled immunoassay (see U.S. Pat. No. 4,238,565), the enzyme modulator-labeled immunoassay, e.g., using inhibitor labels (see U.S. Pat. Nos. 4,134,972 and 4,273,866), and enzyme-labeled immunoassay (see U.S. Pat. No. 3,817,837).

The antibody reagent of the present invention is characterized by its specific binding affinity for a linear peptide epitope in the particular protein of interest. Therefore, as used herein the term "antibody reagent" will refer to any material however obtained which comprises an antibody combining site specific for such peptide epitope. Such expression therefore includes whole antibodies as well as appropriate fragments or polyfunctionalized forms thereof. When in the form of whole antibody, it can belong to any of the classes and subclasses of known immunoglobulins, e.g., IgG, IgM, and so forth. Any fragment of any such immunoglobulin which retains specific binding affinity for the peptide epitope can also be employed, for instance, the fragments of IgG conventionally known as Fab, Fab', and F(ab')$_2$. In addition, aggregates, polymers, derivatives, conjugates, and hybrids of immunoglobulins or their fragments can be used where appropriate.

The immunoglobulin source for the antibody reagent can be obtained in any available manner such as conventional antiserum and monoclonal techniques. Antiserum can be obtained by well-established procedures involving immunization of an animal, such as a mouse, rabbit, guinea pig, and the like, with an appropriate immunogen. The immunoglobulins can also be obtained through somatic cell hybridization, such resulting in what are commonly referred to as monoclonal antibodies.

Monoclonal antibody reagents are particularly preferred. Hybridoma cell lines are raised to produce antibodies only against the linear peptide epitope portion of the protein molecule rather than to the entire protein and such cell lines and their antibodies are screened to identify and isolate those monoclonal antibodies which will react selectively with the desired epitope.

In one method to produce such antibodies, a fragment of the protein chain, corresponding to and comprising the naturally occurring linear peptide epitope sequence, is coupled to a protein carrier and injected into a laboratory animal to elicit an immune response. Alternatively, the immunogen can comprise a linearized or denatured form of the protein or a fragment thereof. Lymphocytes such as spleen cells from the immunized animal are fused with myeloma cells to produce hybridomas which are cultured and screened for production of monoclonal antibodies. The monoclonal antibodies are screened for those selective to the peptide epitope and the particular cell line is cloned for use in producing further quantities of the monoclonal antibody.

To produce antibodies against a synthetic peptide immunogen in the laboratory animal, e.g., BALB/c mice, rats or the like, a peptide comprising the desired epitope will be produced and isolated from the naturally occurring protein or will be chemically synthesized and purified. Such a protein fragment will include all of the critical amino acid units of the desired epitope and can include additional amino acid units, some or all of which optionally will correspond to the sequence of amino acids in the protein of interest.

To ensure that the epitope-containing peptide fragment is optimally antigenic, it can be advantageously coupled in multiples to an immunogenic carrier material. The immunogenic carrier material can be selected from any of those conventionally known having functional groups available for coupling to the peptide residue. In most cases, the carrier will be a protein or polypeptide, although other materials such as carbohydrates, polysaccharides, lipopolysaccharides, nucleic acids, and the like of sufficient size and immunogenicity can likewise be used. For the most part, immunogenic proteins and polypeptides will have molecular weights between 4,000 and 10,000,000, preferably greater than 15,000, and more usually greater than 50,000. Generally, proteins taken from one animal species will be immunogenic when introduced into the blood stream of another species. Particularly useful proteins are albumins, globulins, hemocyanins, glutelins, and the like. Further reference for the state-of-the-art concerning conventional immunogenic carrier materials and techniques for coupling haptens thereto may be had to the following: Parker, Radioimmunoassay of Biologically Active Compounds, Prentice-Hall (Englewood Cliffs, N.J. USA, 1976); Butler, J. Immunol. Meth. 7: 1–24 (1974); Weinryb and Shroff, Drug Metab. Rev. 10: 271–283 (1974); Broughton and Strong, Clin. Chem. 22: 726–732(1976); and Playfair et al, Br. Med. Bull. 30: 24–31 (1974).

The number of epitopes coupled to a given immunogenic carrier material will be limited only by the number of available coupling sites on the carrier and can be as high as several thousand in the case of certain high molecular weight synthetic polypeptides such as polylysine. The epitopic density on a particular carrier will depend upon the molecular weight of the carrier and the density of available coupling sites. Optimal epitopic densities, considering the ease and reproducibility of synthesis of the immunogen and antibody response, fall between about 10% and about 50% of the available coupling groups on the carrier involved.

The peptide fragments will be coupled to the carrier material by any convenient coupling method. Functional groups on the native amino acids in the fragment or functional groups introduced by chemical modification of the fragment will normally be used to couple directly or through bifunctional coupling agents to functional groups on the carrier. It will be preferred to design the peptide fragment to have a single uniquely reactive functional group for obtaining unambiguous coupling to the carrier.

The present invention will now be illustrated, but is not intended to be limited, by the following specific examples.

EXAMPLE 1

Preparation and characterization of Antibodies to the Glycopeptide Epitope in Hb Alc (a) An 11-amino acid peptide comprising the 8 N-terminal units of beta-hemoglobin plus two units of tyrosine plus a unit of cysteine was synthesized according to Gutte, B. and R. B. Merrifield; J. Am. Chem. Soc., 91: 2,501 (1969), giving the following peptide:

NH$_2$-valine-histidine-leucine-threonine-proline-glutamic acid-glutamic acid-lysine-tyrosine-tyrosine-cysteine-COOH.

To glucosylate this peptide, 200 mg of this purified peptide is reacted with 0.25 molar glucose in 20 ml of anhydrous pyridine for 48 hours at room temperature in the dark. The mixture is dried in vacuum. The resulting syrup is resuspended in 20 millimolar potassium phosphate, pH 2.95, and purified by HPLC.

The glucopeptide-bearing fractions are dissolved in 0.1M triethylammonium acetate pH 8.5 and chromatographed over Affigel-601 boronate affinity resin (Biorad), whereby the glucopeptide is selectively adsorbed. The resin is washed with 0.1M triethylammonium acetate pH 8.5 and the glucopeptide eluted with 0.1M triethylammonium acetate pH 5.0. The eluate is lyophilized.

The product is resuspended in 1 ml of water, reacted with a 500 fold molar excess dithiothreitol (to restore the SH group of the cysteine) and the reduced peptide repurified by HPLC, and lyophilized. This glucopeptide is stored at $-20°$ C. under N$_2$ until further use.

(b) A KLH-MBS conjugate, as previously described, Lerner, R. et al, Proc. Natl. Acad. Sci. 78: 3403(1981) is reacted with the product of (a) in a 2-fold molar ratio of glucopeptide to maleimide on the carrier, in 50 millimolar (mM) potassium phosphate, pH 7.2, for 1 hour at room temperature.

(c) The solution in (b) is mixed with equal volumes of Freund's complete adjuvant to form a water-in-oil emulsion and 200 μg of conjugate is injected into BALB/cBy mice. The mice are boosted at 30 and 60 days, sacrificed, and their spleens used for fusion according to Kohler and Milstein, Nature 256: 495(1975), producing numerous hybridomas. The hybridomas are screened to identify those which produced monoclonal antibodies specific for the glucosylated peptide epitope.

The screening for A$_{1c}$ specific monoclonal antibodies is conducted using an ELISA format, where the antigen is absorbed onto polystyrene microtiter plates (Linbro). The antigens are purified human A$_{1c}$ and non-glucosylated Ao hemoglobin. The A$_{1c}$ is purified from a red blood cell hemolysate using two different chromatographic procedures. The first purification consists of binding glycosylated hemoglobin onto a boronate affinity resin as described by Pierce Chemical Co., Rockford, Ill., U.S.A. product no. 42,000. Typically 1 to 5 grams of hemoglobin are applied to 100 ml boronate resin, and the bound (glycohemoglobin) fraction elutes as described by Pierce Chemical Co., GlycoTest bulletin, product no. 42,000. The eluted glycohemoglobin fraction is equilibrated in low ionic strength buffer and chromatographed on an ion-exchange resin as described by McDonald, M. et al, J. Biol. Chem., 253: 2327-2332(1978). The A$_{1c}$ "peak" is analyzed by isoelectric focusing and by carbohydrate analysis using the thiobarbituric acid assay and the results confirm that this purification produced ultrapure A$_{1c}$ hemoglobin in that the purified material has both carbohydrate and differed from normal Ao hemoglobin in isoelectric point. Similarly, Ao hemoglobin as purified by its property of not binding to the boronate affinity resin and chromatographing by ion-exchange as the Ao "peak" on the ion-exchange chromatographic purification. The pure A$_{1c}$ and Ao hemoglobins are adsorbed onto separate microtiter plates (2 μg per 100 microliters PBS per well) overnight at 4° C. The plates are blocked in 1% BSA in PBS for 60 minutes at room temperature then washed 4 times in PBS. Supernatant from each hybridoma cell line is added to the A$_{1c}$ and Ao plate and incubated at room temperature for 60 minutes. The plates are washed 4 times in PBS and a secondary antibody (rabbit-anti-mouse IgG-peroxidase, Miles Laboratories, Inc., Elkhart, Ind. U.S.A. at a 1:5000 dilution in 1% BSA in PBS) is applied and is subject to incubation for 60 minutes at room temperature. The plate is washed 4 times in PBS and 200 microliters of a substrate solution added (24.3 mM citric acid, 51.4M sodium phosphate, pH 5.3 containing 2.2 mM M o-phenylenediamine and 5.2 mM hydrogen peroxide). The reaction is terminated after 20 minutes by adding 50 microliters of 8M H$_2$SO$_4$ and the product of the peroxidase reaction is read at 492 mM.

From 200 starting hybridomas producing antibodies against hemoglobin, nine (9) are identified as being specific for the A$_{1c}$ epitope, whereas 191 reacts both with A$_{1c}$ and non-glucosylated hemoglobin. Since pre-immunized mouse serum has no detectable antibody response to Ao or A$_{1c}$ human hemoglobin by the ELISA procedure, the major immune response is against the eight peptide sequence that is shared in common with A$_{1c}$ and Ao. Since the synthetic peptide immunogen consists of eight amino acid residues, of the hemoglobin sequence, the major mouse immune response is directed against the peptide, and not the carbohydrate (191 of the 200 hybridomas reacting both with Ao and A$_{1c}$). As expected, the immunized mouse serum also has broadly cross reacting antibodies reactive both with Ao and A$_{1c}$ suggesting that no specificity for A$_{1c}$ is obtained unless hybridomas are screened for reactivity against A$_{1c}$ and not against Ao hemoglobin. The preferred hybridomas producing antibodies against A$_{1c}$ hemoglobin and not against Ao hemoglobin, were deposited with ATCC identified as ATCC HB 8639 and ATCC HB 8869, deposited on Oct. 11, 1984 and July 10, 1985, respectively.

(d) Identification of the peptides that compete with A$_{1c}$ for binding to antibody:

The following peptides are generated by enzyme digestion of the glucosylated 11-amino acid parent peptide Glyco-Val-His-Leu-Thr-Pro-Glu-Glu-Lys-Tyr-Tyr-Cys (GLYCOPEPTIDE 1)

All peptide fragments are purified by HPLC and quantitated by amino acid analysis. Tryptic digestion of the parent peptide produced Glyco-Val-His-Leu-Thr-Pro-Glu-Glu-Lys. (GLYCOPEPTIDE 2)

A proline specific endoprotease produces Glyco-Val-His-Leu-Thr-Pro. (GLYCOPETIDE 3) The peptide Glyco-Val-His-FAD (GLYCOPEPTIDE 4) wherein the dipeptide is coupled to N$^6$-aminohexyl FAD and then glucosylated is made by the method of Carrico and Johnson, U.S. Pat. No. 4,255,566 and provided by Dr. Kin Yip and Dr. R. Buckler, Ames Division, Miles Laboratories, Inc., Elkhart, Ind. U.S.A.

Figure 2:
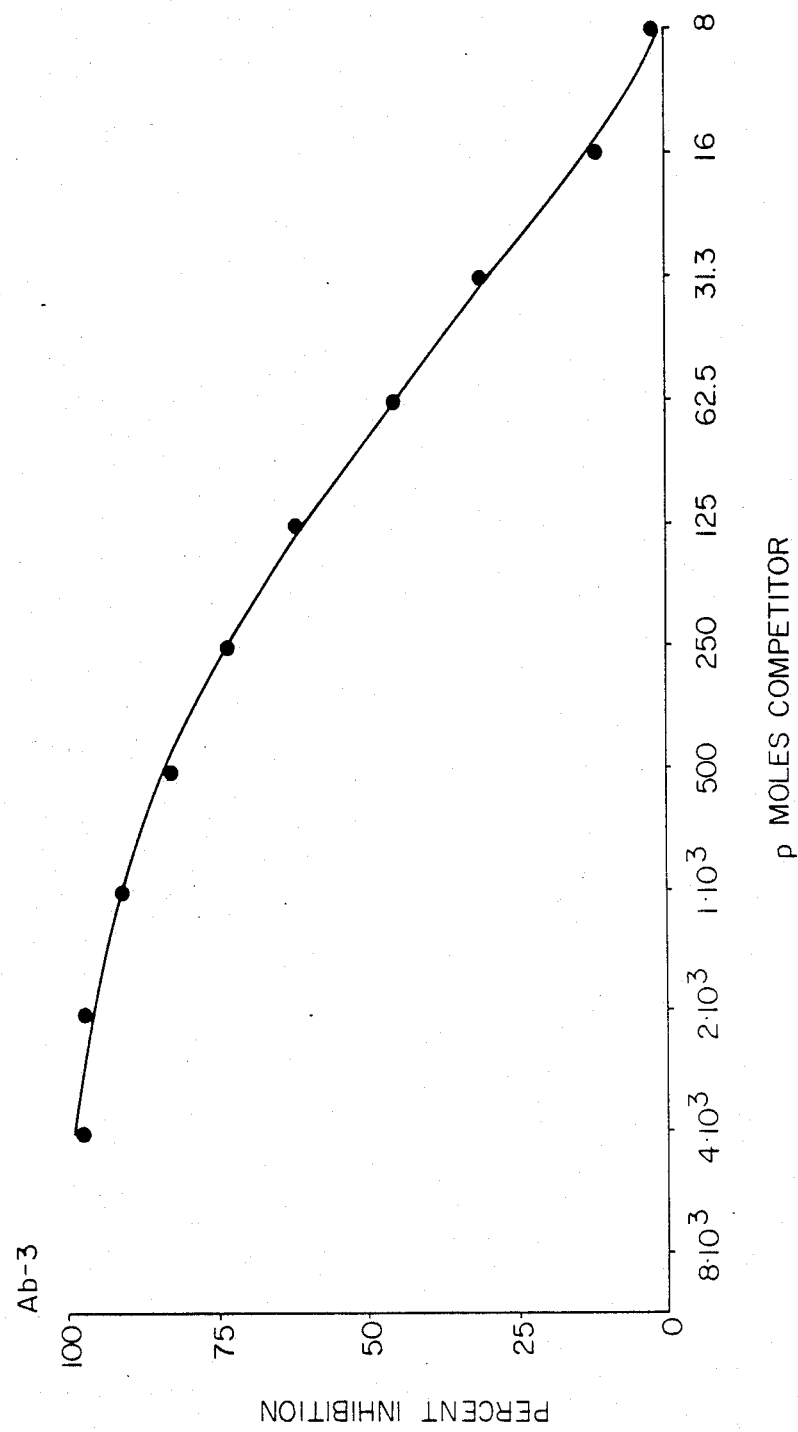
FIG. 2 is a plot depicting the inhibition of Ab-3 binding to $A_{1c}$ by glycopeptide 3 (PEPTIDE 3). The competitive experiment was done as described for FIG. 1.
Figure 3:
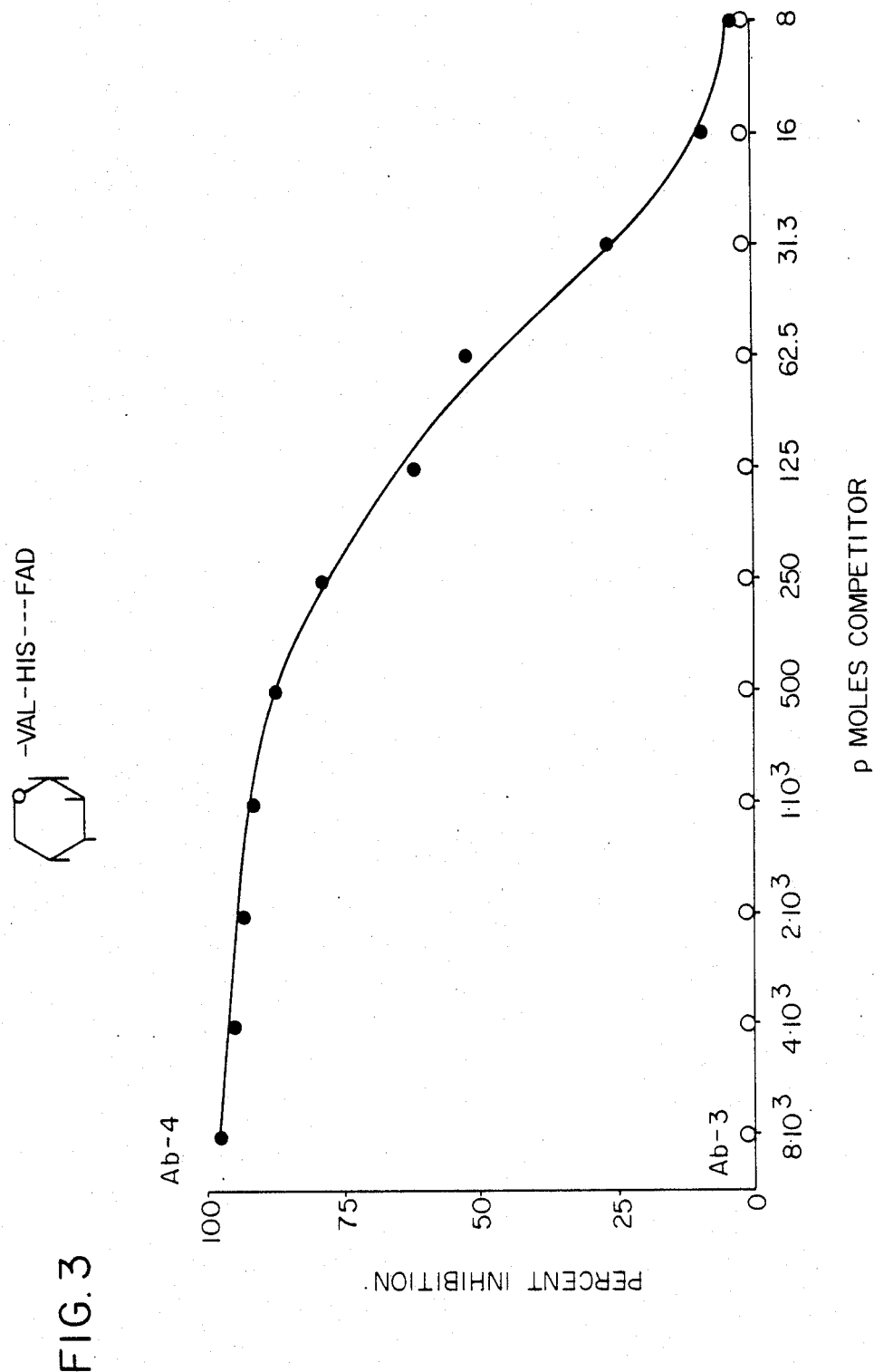
FIG. 3 is a plot depicting the inhibition of Ab-3 and Ab-4 by glycopeptide 4 (PEPTIDE 4) for $A_{1c}$ binding. The competition experiment was conducted as described for FIG. 1.

In a typical competition assay, each peptide 8 nanomoles to 8 picomoles in 100 μl PBS-7.2 mM Na$_2$HPO$_4$, 2.8 mM NaH$_2$PO$_4$, 127 mM NaCl, pH 7.4 is incubated with 100 μl monoclonal cell culture supernatant for 60 minutes at room temperature. This mixture is added to a polystyrene microtiter plate coated with 1 μg A$_{1c}$ hemoglobin/well. If the peptide completes with the antibody, the antibody is not free to bind to the immobilized A$_{1c}$. The plate is washed four times with PBS. A second antibody (rabbit anti mouse IgG coupled with horseradish peroxidase) is added for 30 minutes and the plate is washed with PBS. The substrate (o-phenylenediamine 2.2 mM), and hydrogen peroxide (0.012%) are added and the color produced measured at 492 nm. The quantitation of the product reflects the extent of competition, e.g., no product indicates that the competing peptide totally blocked the antibody from binding to the immobilized A$_{1c}$. The results indicate that all four of the previously described glycopeptides including Glyco-Val-His-FAD are effective competitors. One of the antibodies, Ab-4, is totally blocked from binding to A$_{1c}$ by GLYCOPEPTIDES 1 to 4 (see FIGS. 1-3). Another antibody, Ab-3, is blocked by GLYCOPEPTIDES 1 to 3, but not by GLYCOPEPTIDE 4 (see FIGS. 1-3).

Peptides lacking the carbohydrate show no competition inhibition suggesting that the carbohydrate is an essential component of the epitope and provides the specificity for the antibodies' recognition of A$_{1c}$ homoglobin (see FIG. 1).

EXAMPLE 2

Competitive Immunoassay for Hb Alc

This competitive immunoassay is based on the use of a fixed amount of hapten-label (as described in Example 5) that competes with A$_{1c}$ in lysed whole blood for binding to the immobilized antibody. Since the antibody recognizes both the A$_{1c}$ and hapten, the level of A$_{1c}$ in the specimen determines the amount of hapten-label that binds to the antibody. Since the antibody is immobilized, all non-bound reactants can be removed by a simple washing step. The bound label can then be measured and compared to a standard for quantitation of A$_{1c}$ in the original blood samples.

The assay is developed using whole blood as the specimen and can be divided into the steps listed below:

(1) Lysis of cells-denaturation of hemoglobin

Since the final assay requires less than 0.3 microliters of whole blood, an accurately pipettable volume of blood (5–50 μl from a finger stick or from whole blood) is diluted into a denaturing solution (3M quanidine HCl, 10 mM Tris-HCl pH 7.5) and heated to 56° C. for 2 to 15 minutes. Lower temperature also work, but additional time is required for the complete denaturation of the sample. The denaturation (a) Inactivates the clotting mechanisms if samples are not prepared in anticoagulants; (b) lyses the red cells; (c) denatures proteases, enzymes etc., and optimally exposes the A$_{1c}$ epitope on hemoglobin; (d) appears to either sterilize or inhibit the growth of microorganisms in the denatured blood sample even if the sample is non-aseptically prepared and handled (e.g., blood from a finger stick) and (e) results in a stable clinical sample that can be stored for days at room temperature without effect on the final assay.

(2) Dilution and Competition

An aliquot of the denatured whole blood is pipetted into a 10 fold volume of buffer containing the hapten-label. This effectively dilutes the hemoglobin to the proper concentration for the assay and dilutes the denaturant to a low concentration so as not to perturb the antibody or enzyme activity. The antibody coated bead is then added for a specified amount of time during which the antibody binds either the A$_{1c}$ hemoglobin or the hapten-HRP.

(3) Wash and Read

Following the competitive incubation, the bead is washed and the label read following the addition of an appropriate substrate. The signal is then compared to a standard and the amount of A$_{1c}$ present in the original whole blood sample determined.

The details of the assays used are summarized below:

Bead Coating Procedure

Polystyrene beads (¼ inch diameter with specular finish) are obtained from Precision Ball Company, Chicago, Ill., U.S.A. Lots are screened for beads that provided the lowest variability in multiple immunoassay determinations of the same sample. Prior to coating, beads are washed with absolute methanol followed by water. The methanol wash seemed to significantly lower the correlation of variation for multiple determinations of the same sample. An antibody solution (5 μg antibody/100 μl in 0.2M sodium borate, pH 8.5, 0.02% sodium azide) is then added to the damp beads and the beads rotated overnight at 4° C. The beads are then washed, blocked with 1% BSA in PBS containing 0.02% sodium azide. Typically, 500 to 1000 beads are coated at one time and used for a period of weeks with no evidence of loss of antibody activity. Coating experiments with radioactive antibody indicate that 0.5 μg of antibody binds per bead.

The beads are used in this immunoassay only because of their property of binding relatively high amounts of protein. The hydrophobic absorption of protein onto polystyrene is convenient, but certainly could be replaced by one of several procedures where proteins are covalently attached to polystyrene, functionalized resins, or silica. The polystyrene can also be in the form of a tube or cuvette.

The working protocol is summarized as follows:

(a) Dilute 50 microliters whole blood into 1.0 ml denaturing solution (3M guanidine-HCl, 10 mM Tris pH 7.5), heat to 56° C., 15 minutes, dilute again 100 μl into 1.0 ml denaturant.

(b) Add 50 microliters of the above solution to 0.5 ml phosphate buffered saline (PBS) pH 7.5 containing hapten-HRP. The incubations, washings and enzymatic reactions are conveniently conducted in 48-well polystyrene tissue culture plates.

(c) Add antibody coated bead and incubate 30 minutes at ambient temperature with rocking.

(d) Wash beads with buffer (PBS) (usually 3-1 ml changes).

(e) Add o-phenylenediamine substrate and hydrogen peroxide.

Figure 4:
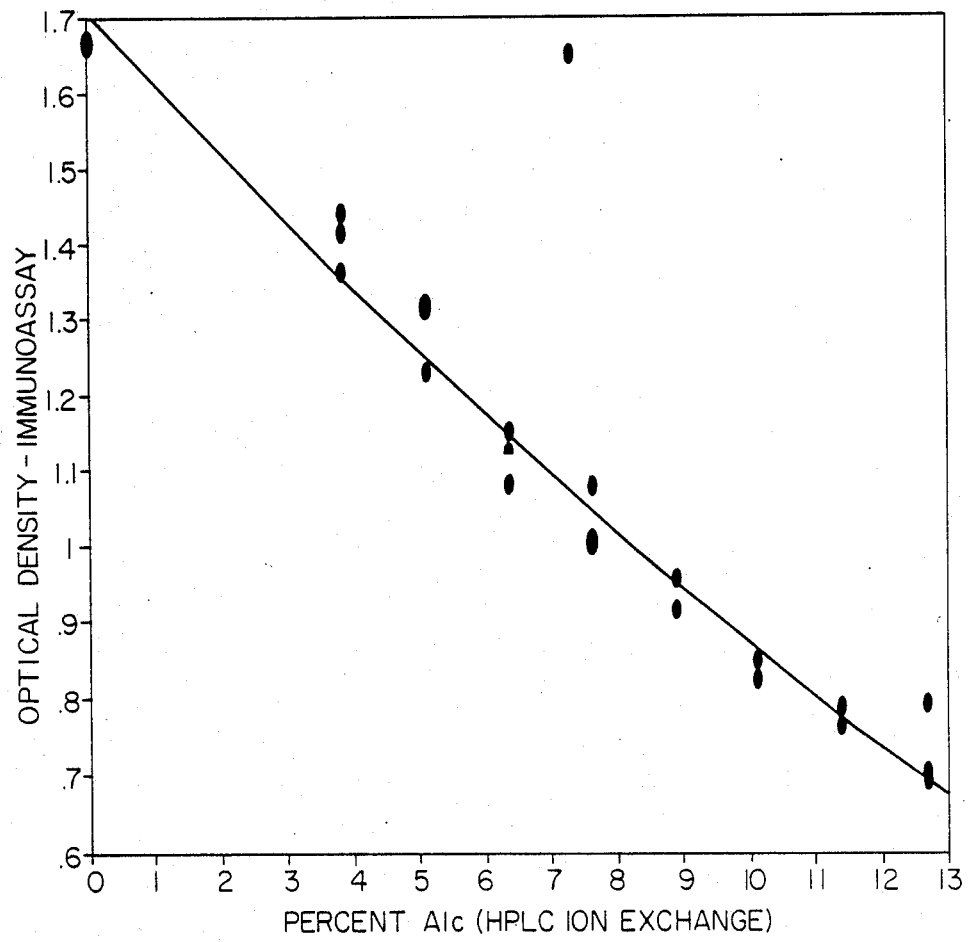
FIG. 4 is a typical standard curve using optimal assay conditions. The whole blood standard was prepared using different ratios of denatured whole blood from a diabetic having 12.66% $A_{1c}$ as measured by HPLC ion exchange with whole blood from a normal donor (3.83% $A_{1c}$). All points of triplicate measurements are plotted.
Figure 5:
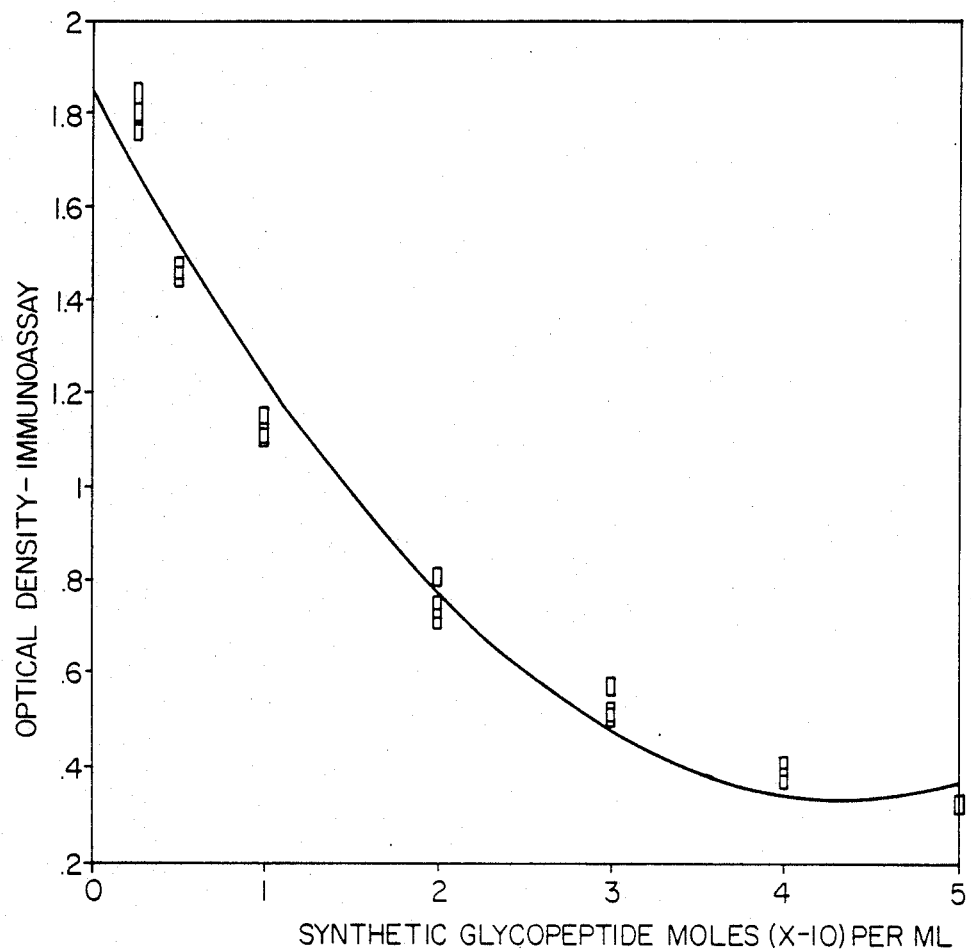
FIG. 5 is a standard curve using a synthetic peptide standard. The assay was performed as described for FIG. 4, except that instead of using whole blood, different amounts of synthetic glycopeptide were used as the competitor. All values of triplicate determinations were plotted.
Figure 6:
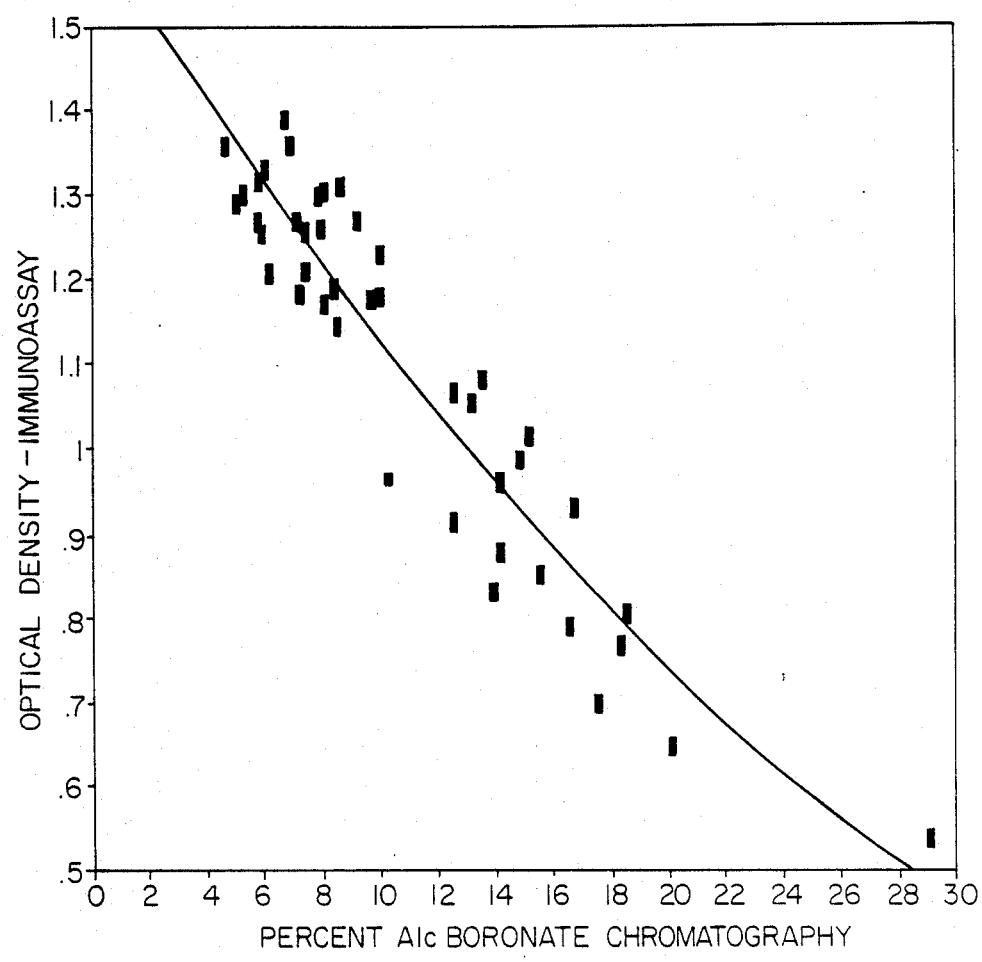
FIG. 6 is a plot depicting a comparison of the immunoassay method with the boronate affinity method for donors. The mean of triplicate determinations are plotted for the immunoassay coordinate.

(f) Stop the reaction and read the product after 20 minutes. The above assay is used in establishing the clinical data described below. The standard curve is shown in FIG. 4. Competition using GLYCOPETIDE 1 is shown in FIG. 5. Evaluation of normal and diabetic donors is shown in FIG. 6. The boronate affinity determination are performed exactly as described by Pierce Chemical Co. (GlycoTest, product no. 42,000).

EXAMPLE 3

Optical exposure of the $A_{1c}$ epitope

Optimal reactivity of the human $A_{1c}$ epitope is seen following treatment of the native hemoglobin (in whole blood or hemolysate) with procedures or reagents which expose the epitope to the antibody combining site. The optimal exposure of the epitope can be accomplished by a physical denaturation (heat, sonication, etc.), by a chemical procedure involving classical denaturants (urea, guanidine, SDS, protease) or by a combination of physical and chemical procedures. Most effective is a procedure in which whole blood (50 microliters) is added to a 1 ml solution of 3M guanidine hydrochloride, 10 mM Tris-HCl, pH 7.4 and heated to 56° C. for greater than one minute. The resulting sample works optimally in subsequent immunoassays for the $A_{1c}$ epitope. The solution can be diluted ten fold in buffer, effectively diluting the guanidine to 0.3M, a concentration that has little if any effect on normal antibody-antigen interactions and enzyme activities, providing a suitable media for subsequent immunoassays.

Figure 7:
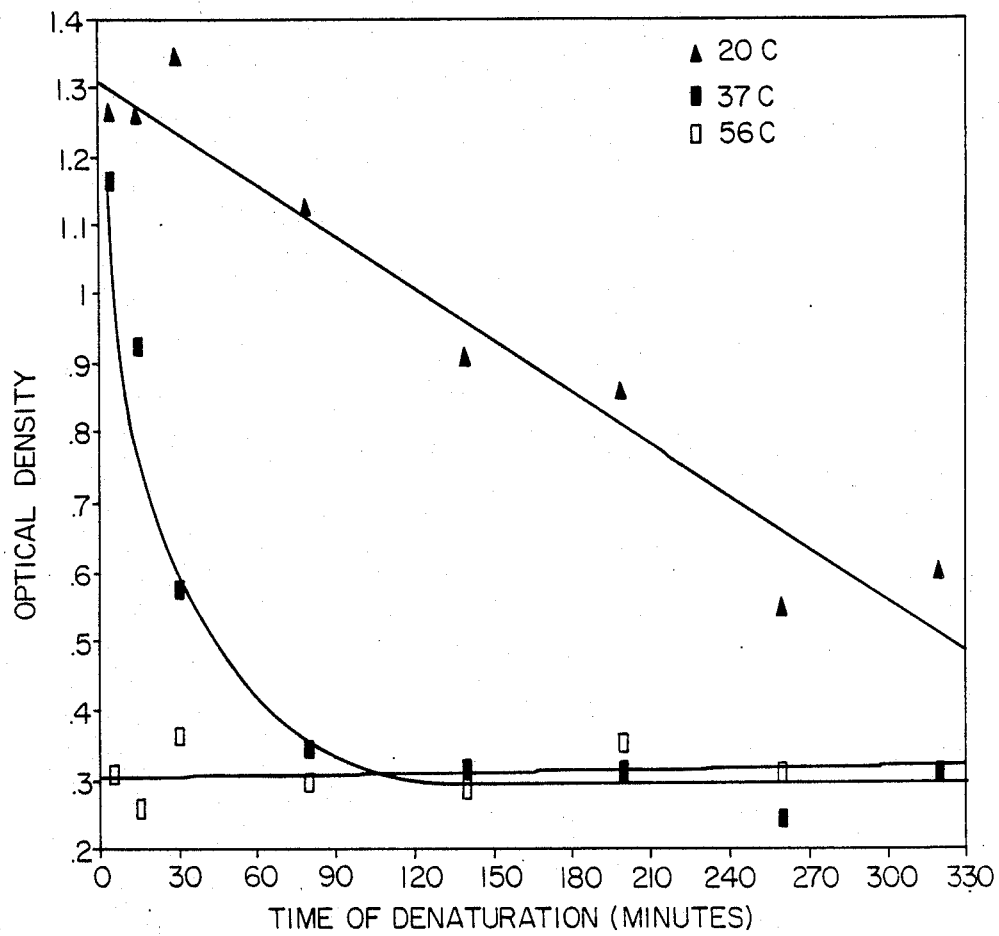
FIG. 7 is a plot demonstrating the exposure of the HB A1c epitope under varying denaturation conditions.

The competitive immunoassay of Example 2 is used. The competitor is the $A_{1c}$ present in whole blood from a diabetic. The whole blood sample is placed in 3.0M guanidine at 20° C., 37° C. or 56° C. for periods of time from 0-320 minutes. The results (FIG. 7) show that with time at 20° C. or 37° C. the epitope is exposed and thus effectively competes with the hapten-HRP conjugate. At 56° C. the epitope is maximally exposed after 5 minutes, the earliest point determined in this assay. The results show that in the native homoglobin $A_{1c}$ tetramer the epitope is buried and inaccessible and does not compete with the linear synthetic glycopeptide-HRP conjugate. However, if homoglobin $A_{1c}$ is denatured, the newly exposed epitope becomes an effective competitor for the linear glycopeptide-enzyme conjugate.

EXAMPLE 4

Figure 8:
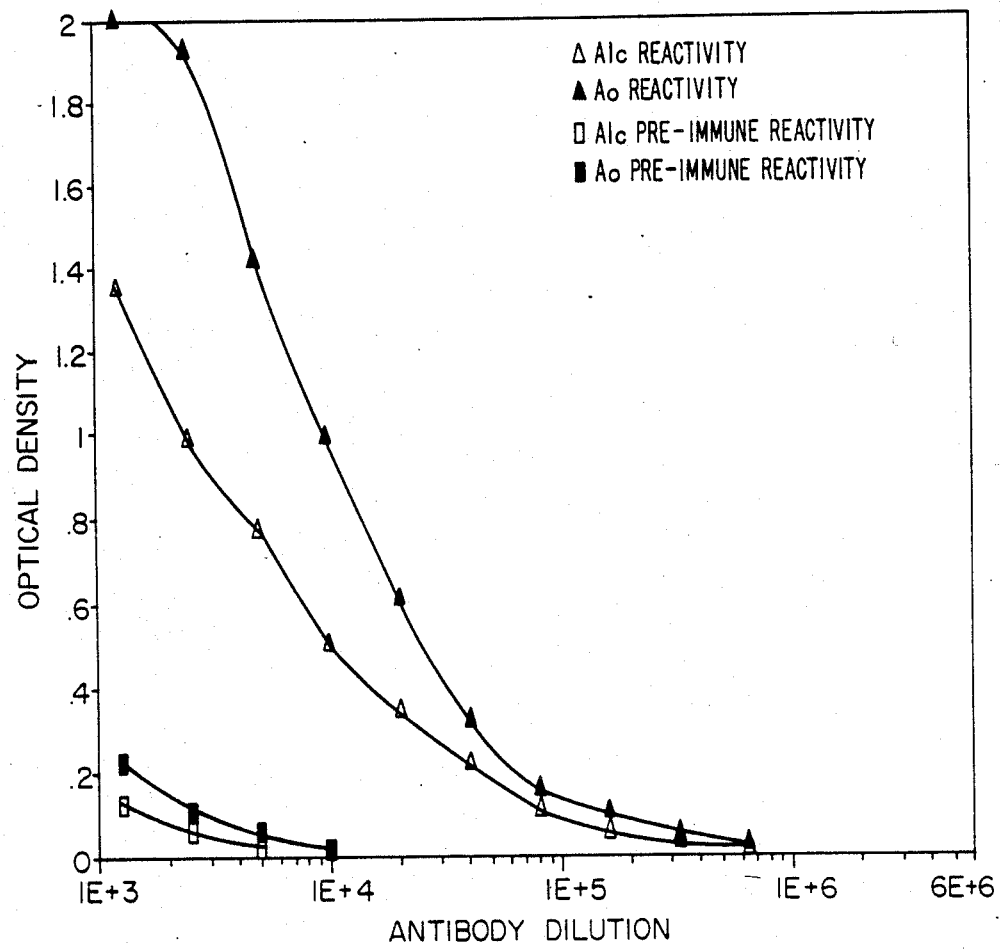
FIG. 8 is a plot depicting the results of immunizing a sheep with the synthetic glycopeptide of Example 1(b).
Figure 9:
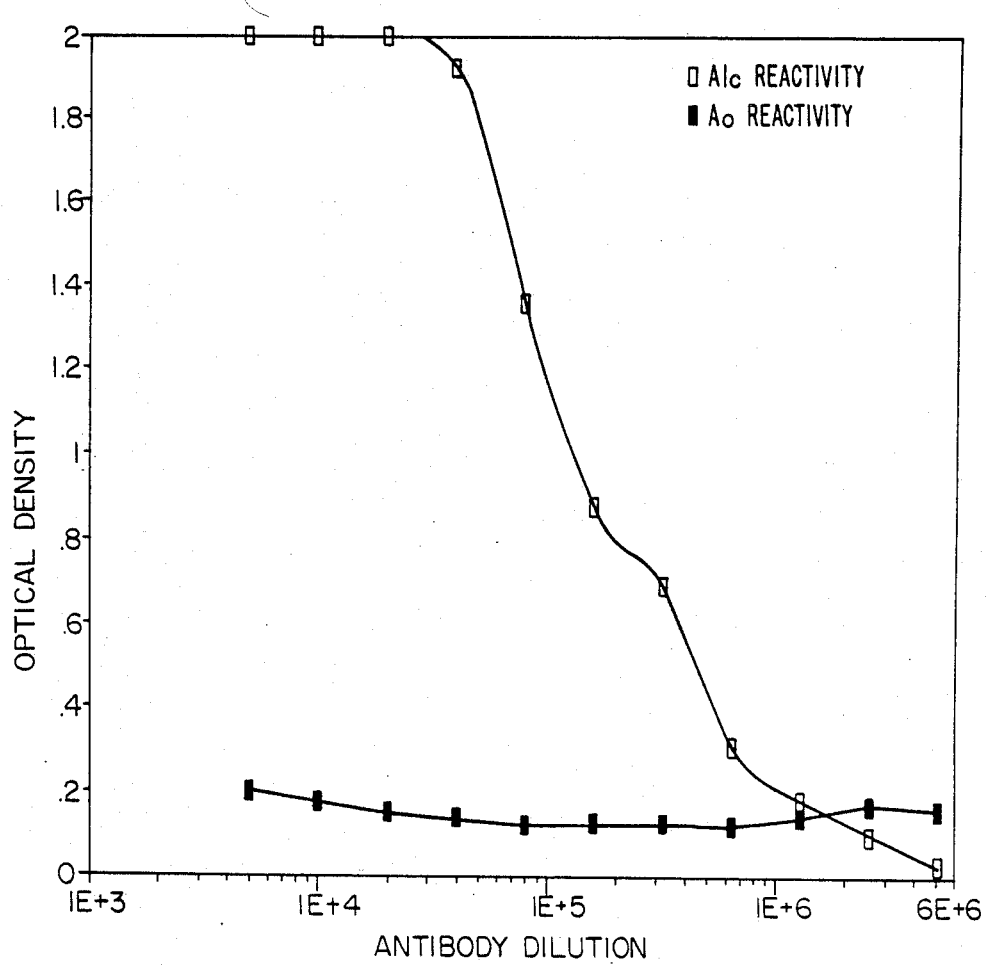
FIG. 9 is a plot demonstrating that mouse monoclonal antibodies are specific for $A_{1c}$ hemoglobin.

Comparison of Antibody Specificity-Sheep Polyclonal vs. Mouse Monoclonal Response A sheep is immunized, 5 sites, IM in Freund's complete adjuvant with the glycopeptide-KLH conjugate (4 mg) of example 1(b). Boost injections are done similarly after 30 days 60 days. The 60 day boost is in Freund's incomplete adjuvant. Preimmune serum, and immune serum is titered for its $A_{1c}$ and Ao specificity in an ELISA assay as described in Example 1(c). The results, (see FIG. 7) show that the synthetic glycopeptide stimulates an immune response against human hemoglobin, but that the immunoglobulins are not specific for $A_{1c}$ hemoglobin. In contrast, mouse monoclonal antibodies for $A1_c$ are quite specific for $A_{1c}$ when measured in the same assay (the ELISA assay of Example 1c—see FIG. 8). Attempts to immunoaffinity purify antibody specific for $A1_c$ from the sheep antiserum were not successful.

EXAMPLE 5

Preparation of Hapten-Label Conjugates

A conjugate of the GLYCOPEPTIDE 1 (HRP) was prepared. The hapten-HRP conjugate was prepared by reacting 15 mg horseradish peroxidase (HRP) with a 10×molar excess of MBS (see Example 1b) in 50 mM sodium phosphate, 1 mM EDTA, pH 7.0. The MBS-HRP conjugate was purified by gel filtration (using the above buffer) and 0.34 mg of the glycopeptide hapten (PEPTIDE 1) was added. The final hapten-HRP conjugate was purified by gel filtration on HPLC and was used at a dilution of 1:100–1:100,000 in the competitive immunoassay of Example 3.

It will be understood that the specification and examples are illustrative, but not limitative of the present invention and that other embodiments within the spirit and scope of the invention will suggest themselves to those skilled in the art.

What is claimed is:

1. A method for binding a particular native protein with an antibody reagent comprising the steps of treating the protein to denature a significant amount thereof and contacting the denatured protein with an antibody reagent specific for binding a linear peptide epitope in such particular protein.

2. The method of claim 1 wherein the linear peptide epitope comprises a sequence of at least two amino acids.

3. The method of claim 2 wherein the linear peptide epitope comprises a sequence of less than 15 amino acids.

4. The method of claim 1 wherein the epitope appears at an N- or C-terminus of a peptide chain in such protein.

5. The method of claim 4 wherein the epitope comprises a non-peptide group.

6. The method of claim 1 wherein the epitope appears along an internal peptide chain in such protein.

7. The method of claim 6 wherein the epitope comprises a non-peptide group.

8. The method of claim 1 wherein the linear peptide epitope is substantially inaccessible to antibody binding in the native protein and the denaturation step is carried out to be sufficient to expose at least the region of the peptide epitope in the protein to make it sufficiently accessible for detectable antibody binding.

9. The method of claim 1, wherein the linear peptide epitope in the native protein is capable of limited detectable binding by the antibody reagent and the denaturation step is carried out to be sufficient to increase exposure at least in the region of the peptide epitope in the protein such that there is an increase in the detectable binding by the antibody reagent.

10. An immunoassay method for determining a particular protein analyte in an aqueous test sample, comprising the steps of treating the test sample to denature a significant amount of any such protein in the sample, contacting the denatured sample with an antibody reagent specific for binding a linear peptide epitope in such particular protein, and determining binding of the antibody reagent to such protein.

11. The method of claim 10 wherein the linear peptide epitope comprises a sequence of at least two amino acids.

12. The method of claim 11 wherein the linear peptide epitope comprises a sequence of less than 15 amino acids.

13. The method of claim 10 wherein the epitope appears at an N- or C-terminus of a peptide chain in such protein.

14. The method of claim 13 wherein the epitope comprises a non-peptide group.

15. The method of claim 10 wherein the epitope appears along an internal peptide chain in such protein.

16. The method of claim 15 wherein the epitope comprises a non-peptide group.

17. The method of claim 10 wherein the linear peptide epitope is substantially inaccessible to antibody binding in the native protein and the denaturation step is carried out to be sufficient to expose at least the region of the peptide epitope in the protein to make it sufficiently accessible for detectable antibody binding.

18. The method of claim 10 wherein the linear peptide epitope in the native protein is capable of limited detectable binding by the antibody reagent and the denaturation step is carried out to be sufficient to increase exposure at least in the region of the peptide epitope in the protein such that there is an increase in the detectable binding by the antibody reagent.

19. The method of claim 10 wherein the denaturation step is accomplished by combining the aqueous test sample with an aqueous solution of a chaotrope present at sufficient concentration and at a sufficient temperature to denature a significant amount of any of the particular protein analyte in the resulting mixture.

20. The method of claim 19 wherein the resulting denatured mixture is maintained at a temperature and diluted sufficiently to reduce the concentration of the chaotrope to a level that has no significant denaturing effect on the antibody reagent subsequently contacted with the mixture, while maintaining the temperature and concentration of the chaotrope sufficiently high to substantially prevent renaturation of any denatured form of the protein analyte that had been produced.

21. The method of claim 19 wherein the chaotrope is selected from the group consisting of guanidine, sodium dodecylsulfate, and urea.

22. The method of claim 20 wherein the chaotrope is selected from the group consisting of guanidine, sodium dodecylsulfate and urea.

23. The method of claim 20 wherein the chaotrope is guanidine and is present in the mixture of the test sample and the chaotropic aqueous solution at a concentration greater than about 3 molar and in the diluted mixture at a concentration less than about 1 molar.

24. The method of claim 10 wherein the antibody reagent is derived from immunization of an animal with a synthetic peptide immunogen comprising a residue of the linear peptide epitope linked to an immunogenic carrier material.

25. The method of claim 24 wherein the antibody reagent is obtained by a monoclonal technique.

26. The method of claim 10 wherein the aqueous test sample is a biological fluid.

27. The method of claim 26 wherein the protein analyte is a glycosylated protein.

28. The method of claim 27 wherein such glycosylated protein is a glucosylated hemoglobin or albumin.

29. The method of claim 10 according to a competitive binding technique wherein the test sample is also contacted with a labeled reagent capable of being bound by said antibody reagent, and the amount of resulting labeled reagent bound to the protein analyte or unbound thereto is determined.

30. The method of claim 29 wherein the labeled reagent is a labeled form of said linear peptide epitope.

31. The method of claim 10 according to a sandwich technique wherein the test sample is contacted with first and second antibody reagents specific for binding mutually exclusive linear peptide epitopes respectively, one of such antibody reagents being labeled, and the amount of the labeled one of the two antibody reagents that is present in the complex of the protein analyte which is bound to each of the two antibody reagents is determined.

32. A reagent system for the immunoassay determination of a particular protein analyte in an aqueous test sample, comprising:
(1) an antibody reagent specific for binding a linear peptide epitope in such particular protein, and
(2) a chemical agent capable of denaturing a significant amount of any such protein in the sample.

33. The reagent system of claim 32 wherein the linear peptide epitope comprises a sequence of at least two amino acids.

34. The reagent system of claim 33 wherein the linear peptide epitope comprises a sequence of less than 15 amino acids.

35. The reagent system of claim 32 wherein the epitope appears at an N- or C-terminus of a peptide chain in such protein.

36. The reagent system of claim 35 wherein the epitope comprises a non-peptide group.

37. The reagent system of claim 32 wherein the epitope appears along an internal peptide chain in such protein.

38. The reagent system of claim 37 wherein the epitope comprises a non-peptide group.

39. The reagent system of claim 32 wherein the chemical agent is a chaotrope.

40. The reagent system of claim 39 wherein the chaotrope is selected from the group consisting of guanidine, sodium dodecylsulfate, and urea.

41. The reagent system of claim 32 wherein the antibody reagent is derived from immunization of an animal with a synthetic peptide immunogen comprising a residue of the linear peptide epitope linked to an immunogenic carrier material.

42. The reagent system of claim 41 wherein the antibody reagent is obtained by a monoclonal technique.

43. The reagent system of claim 32 wherein the aqueous test sample is a biological fluid.

44. The reagent system of claim 43 wherein the protein analyte is a glycosylated protein.

45. The reagent system of claim 44 wherein such glycosylated protein is glucosylated hemoglobin or albumin.

46. The reagent system of claim 32 which additionally comprises a labeled reagent capable of being bound by said antibody reagent.

47. The reagent system of claim 46 wherein the labeled reagent is a labeled form of said linear epitope.

48. The reagent system of claim 32 which comprises first and second antibody reagents specific for binding mutually exclusive linear peptide epitopes respectively, one of such antibody reagents being labeled.

49. A method of claim 1 wherein the protein is denatured by addition of a chaotropic agent.

50. A method of claim 49 wherein the chaotropic agent is selected from the group consisting of guanidine and urea.

51. A method of claim 49 wherein the chaotropic agent is a detergent.

52. A method of claim 1 wherein the protein is denatured by high pH or low pH.

53. A method of claim 1 wherein the protein is denatured by digestion with a proteolytic enzyme.

54. A method of claim 1 wherein the protein is denatured by heating.

55. A method of claim 1 wherein the protein is denatured by sonication.

56. A method of claim 1 wherein the antibody reagent is derived from immunization of an animal with a synthetic peptide immunogen comprising a residue of the linear peptide epitope linked to an immunogenic carrier material.

57. A method of claim 56 wherein the antibody reagent is obtained by a monoclonal technique.

58. A method of claim 1 wherein the antibody reagent is derived from immunization of an animal with a denatured form of the protein or a fragment thereof comprising the linear peptide epitope.

59. A method of claim 10 wherein the protein is denatured by addition of a chaotropic agent.

60. A method of claim 59 wherein the chaotropic agent is selected from the group consisting of guanidine and urea.

61. A method of claim 59 wherein the chaotropic agent is a detergent.

62. A method of claim 10 wherein the protein is denatured by high pH or low pH.

63. A method of claim 10 wherein the protein is denatured by digestion with a proteolytic enzyme.

64. A method of claim 10 wherein the protein is denatured by heating.

65. A method of claim 10 wherein the protein is denatured by sonication.

66. A method of claim 10 wherein the antibody reagent is derived from immunization of an animal with a denatured form of the protein or a fragment thereof comprising the linear peptide epitope.

67. A reagent system of claim 32 wherein the chemical agent is a detergent.

68. A reagent system of claim 32 wherein the chemical agent is a proteolytic enzyme.

69. A reagent system of claim 32 wherein the antibody reagent is derived from immunization of an animal with a denatured form of the protein or a fragment thereof comprising the linear peptide epitope.

* * * * *

UNITED STATES PATENT AND TRADEMARK OFFICE
CERTIFICATE OF CORRECTION

PATENT NO. : 4,658,022

DATED : April 14, 1987

INVENTOR(S) : William J. Knowles, et al.

Page 1 of 2

It is certified that error appears in the above-identified patent and that said Letters Patent is hereby corrected as shown below:

| | |
|---|---|
| Col. 3, line 28 | Correct spelling of --application-- |
| Col. 4, line 2 | Delete "present" and substitute --percent-- |
| Col. 4, line 32 | Delete "HB" and substitute --Hb-- |
| Col. 4, line 54 | After "since" delete "in" and substitute --an-- |
| Col. 5, line 5 | Delete "asymmetrical" and substitute --asymmetric-- |
| Col. 5, line 58 | Delete "nature" and substitute --native-- |
| Col. 7, line 10 | Correct spelling of --immunogens-- |
| Col. 7, lines 35-36 | Correct spelling of --responsible-- |
| Col. 15, line 7 | Delete "with" and substitute --in-- |
| Col. 15, line 38 | Correct spelling of --quantitation-- |
| Col. 15, line 49 | Delete "temperature" and substitute --temperatures-- |
| Col. 15, line 54 | Delete "$A_{jc}$" and substitute --$A_{1c}$-- |
| Col. 16, lines 63-64 | Correct spelling of --GLYCOPEPTIDE-- |

UNITED STATES PATENT AND TRADEMARK OFFICE
CERTIFICATE OF CORRECTION

PATENT NO. : 4,658,022
DATED : April 14, 1987
INVENTOR(S) : William J. Knowles, et al.

It is certified that error appears in the above-identified patent and that said Letters Patent is hereby corrected as shown below:

Col. 17, line 3           Delete "Optical" and substitute --Optimal--

Col. 17, lines 24, 32, 35  Delete "$A_{lc}$" and substitute --Alc--

Col. 18, line 2           Delete "1:100" and substitute --1:1000--

Signed and Sealed this

Eighteenth Day of August, 1987

Attest:

DONALD J. QUIGG

Attesting Officer    Commissioner of Patents and Trademarks